US009880293B2

(12) United States Patent
Helm et al.

(10) Patent No.: US 9,880,293 B2
(45) Date of Patent: *Jan. 30, 2018

(54) X-RAY IMAGING SYSTEM AND METHOD

(71) Applicant: Medtronic Navigation, Inc., Louisville, CO (US)

(72) Inventors: Patrick A. Helm, Milton, MA (US); Shuanghe Shi, Southborough, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/230,720

(22) Filed: Aug. 8, 2016

(65) Prior Publication Data

US 2016/0341831 A1 Nov. 24, 2016

Related U.S. Application Data

(63) Continuation of application No. 13/078,596, filed on Apr. 1, 2011, now Pat. No. 9,411,057.

(51) Int. Cl.
*A61B 6/00* (2006.01)
*G01T 1/20* (2006.01)
(Continued)

(52) U.S. Cl.
CPC .......... *G01T 1/2018* (2013.01); *A61B 6/4085* (2013.01); *A61B 6/4208* (2013.01);
(Continued)

(58) Field of Classification Search
CPC ............................ A61B 6/4266; A61B 6/4085
See application file for complete search history.

(56) References Cited

U.S. PATENT DOCUMENTS 4,637,040 A 1/1987 Sohval et al.
5,464,984 A 11/1995 Cox et al.
(Continued)

FOREIGN PATENT DOCUMENTS

CN 1127553 A 7/1996
CN 1643371 A 7/2005
(Continued)

OTHER PUBLICATIONS

"Medtronic O-Arm Multi-Dimensional Surgical Imaging System"; Brochure, 24pp, 2009.
(Continued)

*Primary Examiner* — Dani Fox
(74) *Attorney, Agent, or Firm* — Harness Dickey

(57) ABSTRACT

An X-ray imaging system can include an X-ray source that projects a beam of X-ray radiation and an X-ray detector positioned to receive the beam of X-ray radiation at a location. The X-ray detector can include: (i) a monolithic substrate having a first side and a second side opposite the first side, (ii) a scintillation layer arranged upon the first side and including a first region and a second region, the first region having a first X-ray sensitivity and the second region having a second X-ray sensitivity different than the first X-ray sensitivity, and (iii) a photosensor array arranged upon the second side. The X-ray source and X-ray detector can be configured to adjust the location at which the X-ray detector receives the beam of X-ray radiation such that the location is primarily within the first region or the second region.

24 Claims, 6 Drawing Sheets

(51) Int. Cl.
  *G01T 1/161* (2006.01)
  *G01T 1/202* (2006.01)
  *A61B 6/12* (2006.01)

(52) U.S. Cl.
  CPC .......... *A61B 6/4405* (2013.01); *A61B 6/4447* (2013.01); *A61B 6/545* (2013.01); *A61B 6/587* (2013.01); *G01T 1/1612* (2013.01); *G01T 1/202* (2013.01); *A61B 6/12* (2013.01); *A61B 6/4452* (2013.01)

(56) References Cited

U.S. PATENT DOCUMENTS

| | | | |
|---|---|---|---|
| 5,570,403 A * | 10/1996 | Yamazaki | A61B 6/032 378/19 |
| 5,841,832 A | 11/1998 | Mazess et al. | |
| 6,519,314 B1 | 2/2003 | Baba et al. | |
| 6,940,941 B2 | 9/2005 | Gregerson et al. | |
| 6,946,661 B2 | 9/2005 | Vafi et al. | |
| 7,001,045 B2 | 2/2006 | Gregerson et al. | |
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 7,490,982 B2 | 2/2009 | Gregerson et al. | |
| 7,869,559 B2 | 1/2011 | Ikhlef et al. | |
| 2002/0020846 A1* | 2/2002 | Pi | H01L 27/1462 257/88 |
| 2002/0054659 A1 | 5/2002 | Okumura et al. | |
| 2004/0120453 A1 | 6/2004 | Vafi et al. | |
| 2006/0034426 A1* | 2/2006 | Freudenberger | A61B 6/4021 378/125 |
| 2007/0076842 A1 | 4/2007 | Tkaczyk et al. | |
| 2007/0140427 A1 | 6/2007 | Jensen et al. | |
| 2008/0095314 A1 | 4/2008 | Katcha et al. | |
| 2009/0026383 A1 | 1/2009 | Kim et al. | |
| 2010/0059683 A1 | 3/2010 | Lauterbach | |
| 2010/0290690 A1 | 11/2010 | Hartmann et al. | |
| 2012/0250822 A1 | 10/2012 | Helm et al. | |

FOREIGN PATENT DOCUMENTS

| | | |
|---|---|---|
| CN | 1671324 A | 9/2005 |
| EP | 0231037 A1 | 8/1987 |
| EP | 0303730 A2 | 2/1989 |
| JP | H042907 A | 1/1992 |
| JP | H05-34463 | 2/1993 |
| JP | H06-296607 A | 10/1994 |
| JP | 2000-005154 A | 1/2000 |
| JP | 2007-167647 A | 7/2007 |
| JP | 2007-532864 A | 11/2007 |
| WO | WO-9908132 A1 | 2/1999 |
| WO | WO-2005052634 A2 | 6/2005 |
| WO | WO-2009155418 A2 | 12/2009 |
| WO | WO-2010-074030 A1 | 7/2010 |
| WO | WO-2012135644 A2 | 10/2012 |

OTHER PUBLICATIONS

"PAXSCAN® Flat Panel X-ray Imaging", Varian Medical Systems, Brochure, Nov. 11, 2004, 15pp.
1st Chinese Office Action dated Apr. 1, 2015 for China Patent No. 20128002665.9.
2nd Chinese Office Action dated Nov. 25, 2015 for CN Application No. 201280026665.9.
3rd Chinese Office Action dated Jun. 15, 2016 for Chinese Patent Application No. 201280026665.9 for corresponding PCT/US2012/031499 claiming benefit of U.S. Appl. No. 13/078,596, filed Apr. 1, 2011.
International Preliminary Report on Patentability and Written Opinion for PCT/US2012/031499 dated Oct. 1, 2013 claiming benefit of U.S. Appl. No. 13/078,596, filed Apr. 1, 2011.
International Search Report and Written Opinion dated Oct. 23, 2012 for PCT/US2012/031499 claiming benefit of U.S. Appl. No. 13/078,596, filed Apr. 1, 2011.
Japanese Office Action dated Mar. 25, 2016 for corresponding Japanese Application No. 2014-502841.
Japanese Office Action dated May 7, 2015 for Japanese Patent Document No. 2014-502841.
Korean Office Action dated Aug. 22, 2016 for Korean Patent Application No. 10-2013-7028711 corresponding to PCT/US2012/031499 claiming benefit of U.S. Appl. No. 13/078,596, filed Apr. 1, 2011.
Korean Office Action dated May 8, 2015 for Korean Patent Document No. 9-5-2015-030521250.
Padovani, R., "Basic Principle of Flat Panel Imaging Detectors, Training Course, Digital Projection Radiography", Sentinel Workshop, Trier, Germany, Feb. 16, 2006. 7 pp.
Sprawls, Perry, "Image Characteristics and Quality", Chapter of the web-based edition of The Physical Principles of Medical Imaging, 2nd Ed., a companion textbook to Physical Principles of Medical Imaging Online, Resources for Learning and Teaching, http://www.sprawls.org/resources, printed from website www.sprawls.org/ppmi2/IMGCHAR/#I . . . Jan. 20, 2011. Chapters published in book: Magnetic Resonance Imaging: Principles, Methods, and Techniques, Perry Sprawls, published in 2000 by Medical Physics Publishing, Madison, Wisconsin. ISBN: 9780944838976. 14pp.
Sprawls, Perry, "X-Ray Image Formation and Contrast", Chapter of the web-based edition of The Physical Principles of Medical Imaging, 2nd Ed., a companion textbook to Physical Principles of Medical Imaging Online, Resources for Learning and Teaching, http://www.sprawls.org/resources, printed from website www.sprawls.org/ppmi2/XRAYCON/. . . Jan. 20, 2011. Chapters published in book: Magnetic Resonance Imaging: Principles, Methods, and Techniques, Perry Sprawls, published in 2000 by Medical Physics Publishing, Madison, Wisconsin. ISBN: 9780944838976. 13pp.
4th Chinese Office Action dated Dec. 21, 2016 for CN Application No. 201280026665.9 corresponding to PCT/US2012/031499 claiming benefit of U.S. Appl. No. 13/078,596, filed Apr. 1, 2011.
European Office Action dated Aug. 29, 2017 in corresponding EP Application No. 12716830.0.

* cited by examiner

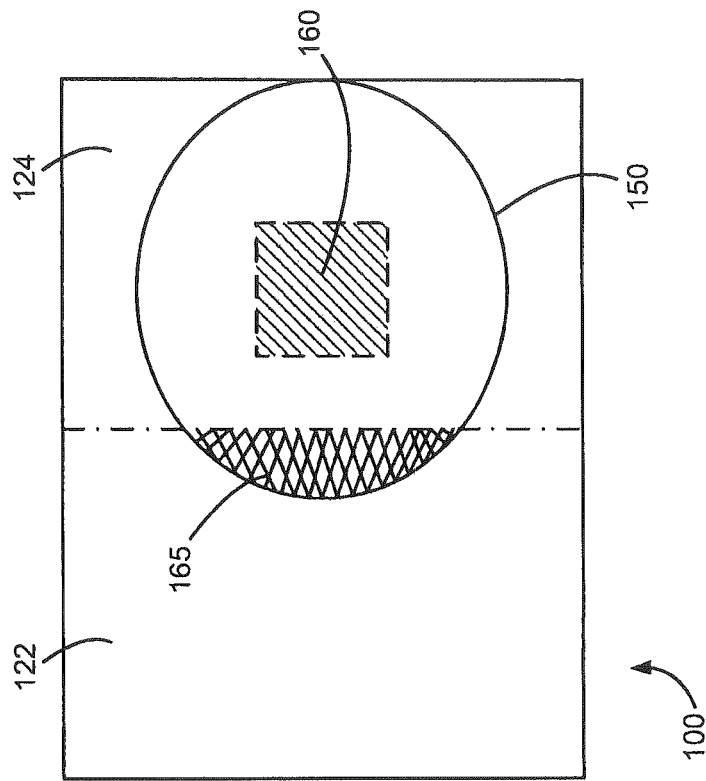
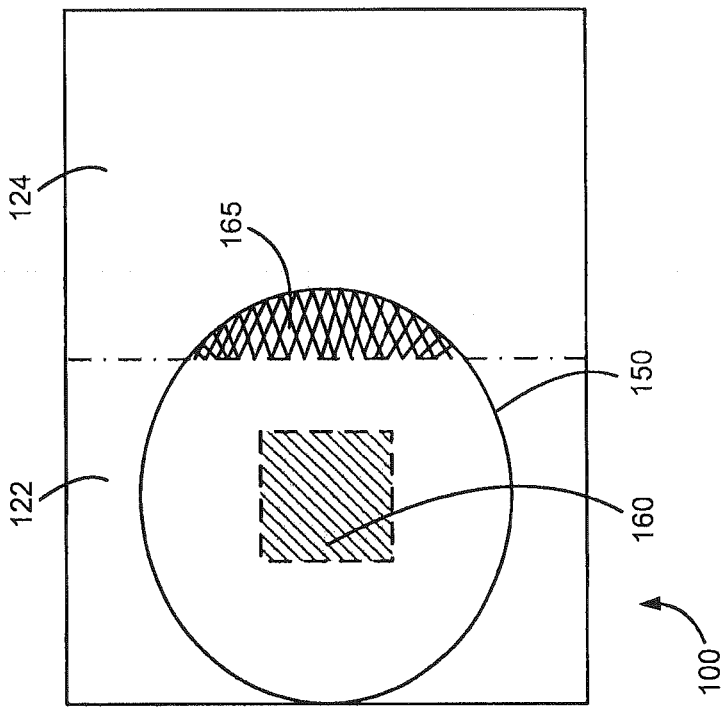

X-RAY IMAGING SYSTEM AND METHOD

CROSS-REFERENCE TO RELATED APPLICATIONS

This application is a continuation of U.S. patent application Ser. No. 13/078,596 filed on Apr. 1, 2011. The disclosure of the above application is incorporated herein by reference.

FIELD

The present disclosure relates to an X-ray imaging system and, more particularly, to an X-ray imaging system that provides different imaging characteristics with a single X-ray detector.

BACKGROUND

This section provides background information related to the present disclosure which is not necessarily prior art.

A subject, such as a human patient, may select or be required to undergo a surgical procedure to correct or augment an anatomy of the patient. The augmentation of the anatomy can include various procedures, such as movement or augmentation of bone, insertion of implantable devices, or other appropriate procedures. A surgeon can perform the procedure on the subject with images of the patient that can be acquired using imaging systems such as a magnetic resonance imaging (MRI) system, computed tomography (CT) system, fluoroscopy (e.g., C-Arm imaging systems), or other appropriate imaging systems.

Images of a patient can assist a surgeon in performing a procedure including planning the procedure and performing the procedure. A surgeon may select a two dimensional image or a three dimensional image representation of the patient. The images can assist the surgeon in performing a procedure with a less invasive technique by allowing the surgeon to view the anatomy of the patient without removing the overlying tissue (including dermal and muscular tissue) when performing a procedure.

SUMMARY

This section provides a general summary of the disclosure, and is not a comprehensive disclosure of its full scope or all of its features.

According to various embodiments, an X-ray imaging system can include an X-ray source that projects a beam of X-ray radiation and an X-ray detector positioned to receive the beam of X-ray radiation at a location. The X-ray detector can include: (i) a monolithic substrate having a first side and a second side opposite the first side, (ii) a scintillation layer arranged upon the first side and including a first region and a second region, the first region having a first X-ray sensitivity and the second region having a second X-ray sensitivity different than the first X-ray sensitivity, and (iii) a photosensor array arranged upon the second side. The X-ray source and X-ray detector can be configured to adjust the location at which the X-ray detector receives the beam of X-ray radiation such that the location is primarily within the first region or the second region.

An imaging method for use with an X-ray imaging system can include positioning a patient between an X-ray source configured to project a beam of X-ray radiation and an X-ray detector to receive the beam of X-ray radiation at a location. The X-ray detector can include: (i) a monolithic substrate having a first side and a second side opposite the first side, (ii) a scintillation layer arranged upon the first side and including a first region and a second region, the first region having a first X-ray sensitivity and the second region having a second X-ray sensitivity different than the first X-ray sensitivity, and (iii) a photosensor array arranged upon the second side. The method can further include adjusting the location to correspond to a region of interest of the patient to be imaged such that at least a portion of the beam of X-ray radiation passes through the region of interest and impinges primarily on the first region. Additionally, the method can include imaging the patient to generate an image having a first image quality for the region of interest of the patient and a second image quality for a portion of the patient other than the region of interest, the first image quality corresponding to the first region and the second image quality corresponding to the second region.

An X-ray imaging system can include an X-ray source that projects a beam of X-ray radiation, an X-ray detector positioned to receive the beam of X-ray radiation at a location and a computing system coupled to the X-ray source and X-ray detector. The X-ray detector can include: (i) a monolithic substrate having a first side and a second side opposite the first side, (ii) a scintillation layer arranged upon the first side and including a first region and a second region, the first region having a first X-ray sensitivity and the second region having a second X-ray sensitivity different than the first X-ray sensitivity, and (iii) a photosensor array arranged upon the second side. The computing system can be configured to generate an image of a patient that is imaged by the X-ray source and X-ray generator. The computing system can include a display device configured to display the image of the patient. The computing system can be further configured to adjust the location to correspond to a region of interest of the patient such that at least a portion of the beam of X-ray radiation is configured to pass through the region of interest and impinge primarily on the first region. The image of the patient can have a first image quality for the region of interest of the patient and a second image quality for a portion of the patient other than the region of interest. The first image quality can correspond to the first region and the second image quality can correspond to the second region.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 8A is a schematic illustration of an exemplary X-ray detector of the imaging system of FIG. 1 with the location of a beam of X-ray radiation in a first position;

FIG. 8B is a schematic illustration of an exemplary X-ray detector of the imaging system of FIG. 1 with the location of a beam of X-ray radiation in a second position;

DETAILED DESCRIPTION

Figure 1:
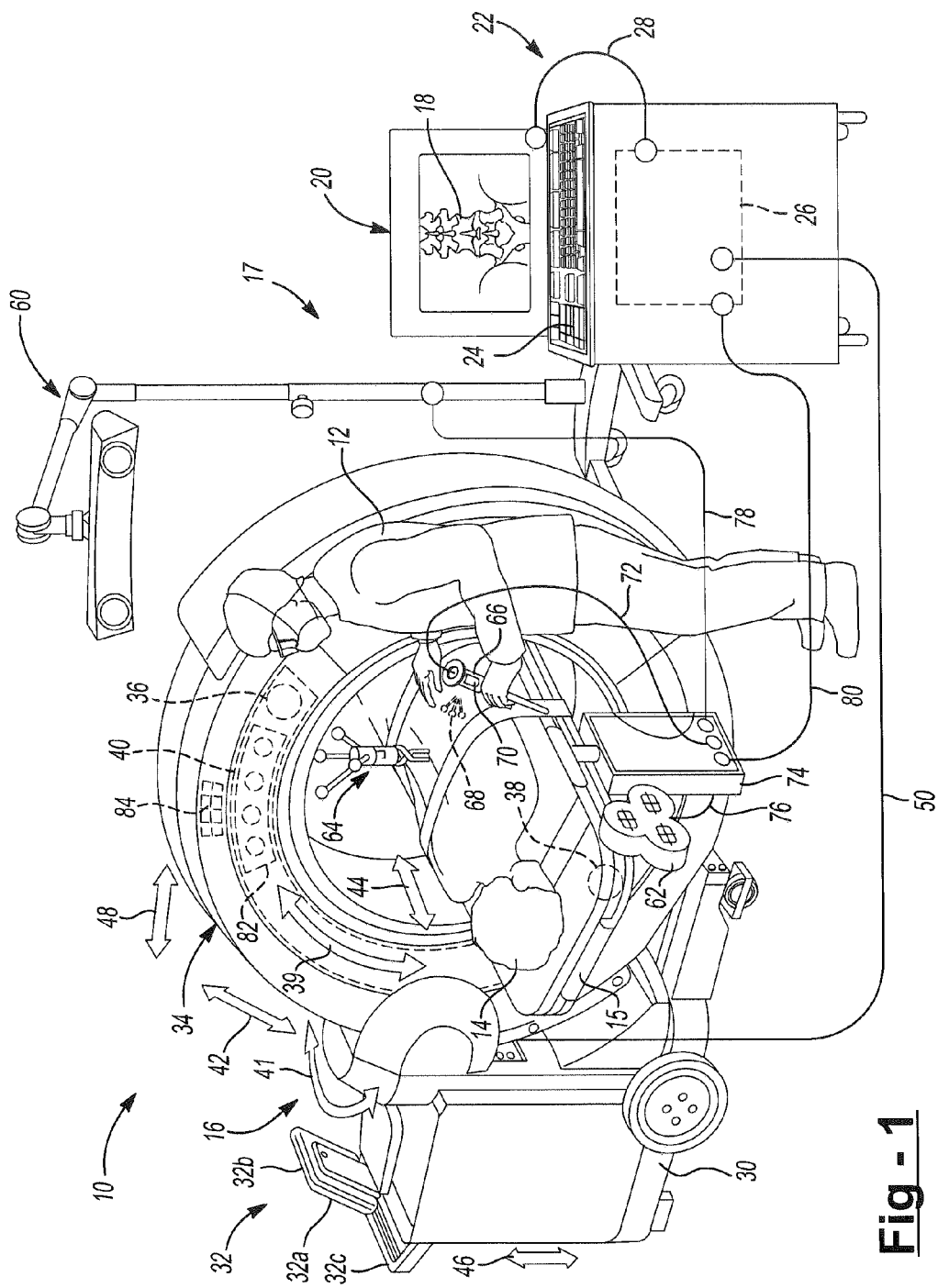
FIG. 1 is an environmental view of an exemplary imaging system according to various embodiments of the present disclosure in an operating theatre.

The following description is merely exemplary in nature. It should be understood that throughout the drawings, corresponding reference numerals indicate like or corresponding parts and features. As indicated above, the present teachings are directed toward an imaging system, such as an O-Arm® imaging system sold by Medtronic Navigation, Inc. having a place of business in Louisville, Colo., USA. It should be noted, however, that the present teachings could be applicable to any appropriate imaging device, such as a C-arm imaging device. Further, as used herein, the term "module" can refer to a computer readable media that can be accessed by a computing device, an application specific integrated circuit (ASIC), an electronic circuit, a processor (shared, dedicated, or group) and memory that executes one or more software or firmware programs, a combinational logic circuit, and/or other suitable software, firmware programs or components that provide the described functionality.

With reference to FIG. 1, in an operating theatre or operating room 10, a user, such as a user 12, can perform a procedure on a patient 14. In performing the procedure, the user 12 can use an imaging system 16 to acquire image data of the patient 14 for performing a procedure. The image data acquired of the patient 14 can include two-dimension (2D) projections acquired with an X-ray imaging system, including those disclosed herein. It will be understood, however, that 2D forward projections of a volumetric model can also be generated, also as disclosed herein.

In one example, a model can be generated using the acquired image data. The model can be a three-dimension (3D) volumetric model generated based on the acquired image data using various techniques, including algebraic iterative techniques, also as discussed further herein. Displayed image data 18 can be displayed on a display device 20, and additionally, could be displayed on a display device 32a associated with an imaging computing system 32, as will be discussed in greater detail herein. The displayed image data 18 can be a 2D image, a 3D image, or a time changing four-dimension image. The displayed image data 18 can also include the acquired image data, the generated image data, both, or a merging of both the types of image data.

It will be understood that the image data acquired of the patient 14 can be acquired as 2D projections, for example with an X-ray imaging system. The 2D projections can then be used to reconstruct the 3D volumetric image data of the patient 14. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can comprise any suitable device to enable a user to interface with the computing system 22, such as a touchpad, touch pen, touch screen, keyboard, mouse, joystick, trackball, wireless mouse, audible controls or a combination thereof. Furthermore, while the computing system 22 is described and illustrated herein as comprising the input device 24 discrete from the display device 20, the computing system 22 could comprise a touchpad or tablet computing device, and further, that the computing system 22 could be integrated within or be part of the imaging computing system 32 associated with the imaging system 16.

A connection 28 can be provided between the computing system 22 and the display device 20 for data communication to allow driving the display device 20 to illustrate the image data 18.

The imaging system 16 can include the O-Arm® imaging system sold by Medtronic Navigation, Inc. having a place of business in Louisville, Colo., USA. It should be noted, however, that the present teachings could be applicable to any appropriate imaging device, such as a C-arm imaging device. The imaging system 16, including the O-Arm® imaging system, or other appropriate imaging systems in use during a selected procedure are also described in U.S. patent application Ser. No. 12/465,206, entitled "System And Method For Automatic Registration Between An Image And A Subject," filed on May 13, 2009, incorporated herein by reference in its entirety. Additional description regarding the O-Arm imaging system or other appropriate imaging systems can be found in U.S. Pat. Nos. 7,188,998, 7,108,421, 7,106,825, 7,001,045 and 6,940,941, each of which is incorporated herein by reference in their entirety.

The imaging system 16 can include a mobile cart 30 that includes the imaging computing system 32 and an imaging gantry 34 in which is positioned an X-ray source 36 and an X-ray detector 100. With reference to FIG. 1, the mobile cart 30 can be moved from one operating theater or room to another and the gantry 34 can move relative to the mobile cart 30, as discussed further herein. This allows the imaging system 16 to be mobile so that it can be used in multiple locations and with multiple procedures without requiring a capital expenditure or space dedicated to a fixed imaging system.

Figure 2:
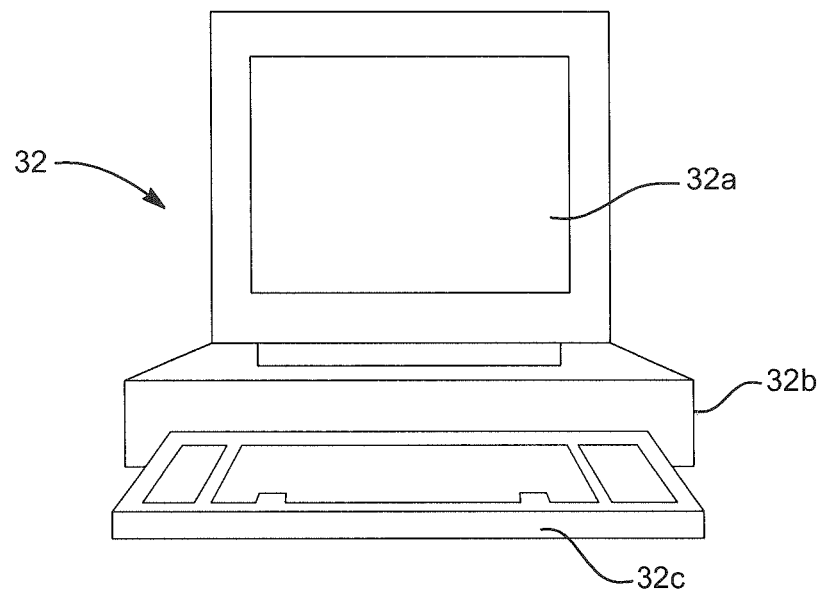
FIG. 2 is a schematic illustration of an exemplary computing system of the imaging system of FIG. 1.

With reference to FIG. 2, a diagram is provided that illustrates an exemplary embodiment of the imaging computing system 32, some or all of the components of which can be used in conjunction with the teachings of the present disclosure. The imaging computing system 32 can include a variety of computer-readable media. The computer-readable media can be any available media that can be accessed by the imaging computing system 32 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 32. The computer-readable media may be accessed directly or through a network such as the Internet.

Figure 3:
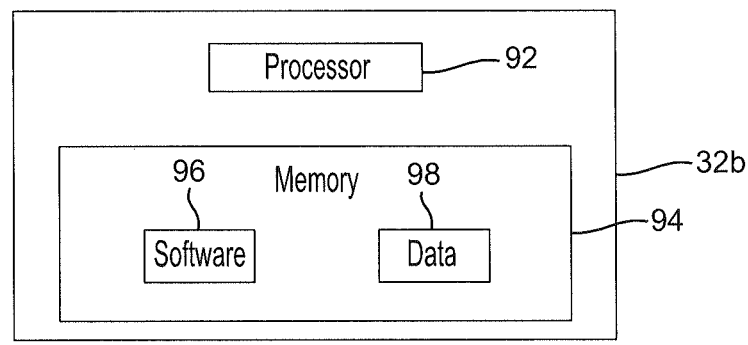
FIG. 3 is a schematic illustration of an exemplary system unit of the computing system of FIG. 2.

In one example, the imaging computing system 32 comprises a display device 32a and a system unit 32b. As illustrated, the display device 32a can comprise a computer video screen or monitor. The imaging computing system 32 can also include at least one input device 32c. The system unit 32b includes, as shown in FIG. 3, a processor 92 and a memory 94, which can include software 96 and data 98.

In this example, the at least one input device 32c comprises a keyboard. It should be understood, however, that the at least one input device 32c can comprise any suitable device to enable a user to interface with the imaging computing system 32, such as a touchpad, touch pen, touch screen, keyboard, mouse, joystick, trackball, wireless mouse, audible controls or a combination thereof. Furthermore, while the imaging computing system 32 is described and illustrated herein as comprising the system unit 32b with the display device 32a, the imaging computing system 32 could comprise a touchpad or a tablet computing device, and the display could employ the display 20.

The imaging computing system 32 can control the source 36, the detector 100 and rotor 40 to enable off-center image data acquisition. A connection can be provided between the processor 92 and the display device 32a for data communication to allow driving the display device 32a to illustrate the image data 18.

With reference to FIG. 1, the source 36 can emit a beam of X-ray radiation through the patient 14 to be detected by the detector 100. As is understood by one skilled in the art, the X-rays emitted by the source 36 can be emitted in a cone and detected by the detector 100. The source 36 and the detector 100 can each be coupled to a rotor 40 so as to be generally diametrically opposed within the gantry 34, and movable within the gantry 34 about the patient 14. Thus, the detector 100 can move rotationally in a 360° motion around the patient 14 generally in the directions of arrow 39, and the source 36 can move in concert with the detector 100 such that the source 36 remains generally 180° apart from and opposed to the detector 100.

In addition, the source 36 can be pivotably mounted to the rotor 40 and controlled by an actuator, such that the source 36 can be controllably pivoted relative to the rotor 40 and the detector 100. By controllably pivoting the source 36, the trajectory of the X-rays can be angled or altered relative to the patient 14, without requiring the patient 14 to be repositioned relative to the gantry 34. Further, the detector 100 can translate about an arc relative to the rotor 40. As the detector 100 can translate, the detector 100 can detect the X-rays emitted by the source 36 at any desired pivot angle, which can enable the acquisition of off-center image data. The rotor 40 can be rotatable about the gantry 34 as needed to acquire the desired image data (on center or off-center). Additional details regarding the mechanics of the movement of the source 36, detector 100 and rotor 40 are disclosed in U.S. Pat. No. 7,108,421, which was previously incorporated by reference above, and U.S. patent application Ser. No. 13/075,446, filed concurrently herewith, entitled "SYSTEM AND METHOD FOR OFF-CENTER IMAGING" to Helm et al., which is incorporated herein by reference in its entirety.

With reference to FIG. 1, the gantry 34 can isometrically sway or swing (herein also referred to as iso-sway) generally in the direction of arrow 41, relative to the patient 14, which can be placed on a patient support or table 15. The gantry 34 can also tilt relative to the patient 14 illustrated by arrows 42, move longitudinally along the line 44 relative to the patient 14 and the mobile cart 30, can move up and down generally along the line 46 relative to the mobile cart 30 and transversely to the patient 14, and move perpendicularly generally in the direction of arrow 48 relative to the patient 14 to allow for positioning of the source 36/detector 100 relative to the patient 14.

The imaging system 16 can be precisely controlled by the imaging computing system 32 to move the source 36/detector 100 relative to the patient 14 to generate precise image data of the patient 14. In addition, the imaging system 16 can be connected with the processor 26 via connection 50 which can include a wired or wireless connection or physical media transfer from the imaging system 16 to the processor 26. Thus, image data collected with the imaging system 16 can also be transferred from the imaging computing system 32 to the computing system 22 for navigation, display, reconstruction, etc.

Briefly, with continued reference to FIG. 1, according to various embodiments, the imaging system 16 can be used with an unnavigated or navigated procedure. In some embodiments, the imaging system 16 can be integrated with a navigation system 17 for performing a navigated procedure. The navigation system 17 can include, e.g., the computing system 22, an optical localizer 60, an electromagnetic localizer 62, a dynamic reference frame 64, an instrument 66, an optical tracking device 68, an electromagnetic tracking device 70, at least one communication line 72, 78, 80, and/or a navigation interface device 74, as further described below. In a navigated procedure, a localizer, including either or both of an optical localizer 60 and an electromagnetic localizer 62 can be used to generate a field or receive or send a signal within a navigation domain relative to the patient 14. The navigated space or navigational domain relative to the patient 14 can be registered to the image data 18 to allow registration of a navigation space defined within the navigational domain and an image space defined by the image data 18. A patient tracker or a dynamic reference frame 64 can be connected to the patient 14 to allow for a dynamic registration and maintenance of registration of the patient 14 to the image data 18.

An instrument 66 can then be tracked relative to the patient 14 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 14 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 14 with use of the registered image data 18 by superimposing an icon/indicia of the instrument 66 on the image data 18 and without direct viewing of the instrument 66 within the patient 14.

Further, the imaging system 16 can include a tracking device, such as an optical tracking device 82 or an electromagnetic tracking device 84 to be tracked with a respective optical localizer 60 or the electromagnetic localizer 62. The tracking device 82, 84 can be associated directly with the source 36, the detector 100, rotor 40, the gantry 34, or other appropriate part of the imaging system 16 to determine the location or position of the source 36, detector 100, rotor 40 and/or gantry 34 relative to a selected reference frame. As illustrated, the tracking device 82, 84 can be positioned on the exterior of the housing of the gantry 34. Accordingly, the imaging system 16 can be tracked relative to the patient 14 as can the instrument 66 to allow for initial registration, automatic registration or continued registration of the patient 14 relative to the image data 18. Registration and navigated procedures are discussed in the above incorporated U.S. patent application Ser. No. 12/465,206.

Figure 4:
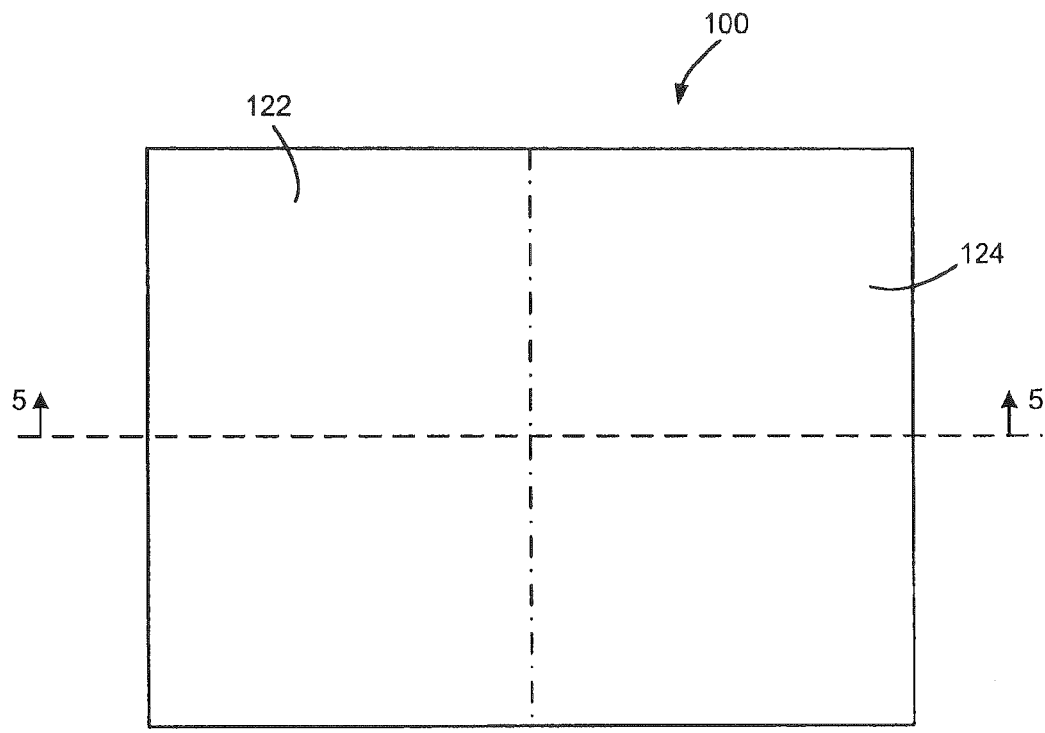
FIG. 4 is a schematic illustration of an exemplary X-ray detector of the imaging system of FIG. 1.
Figure 5:
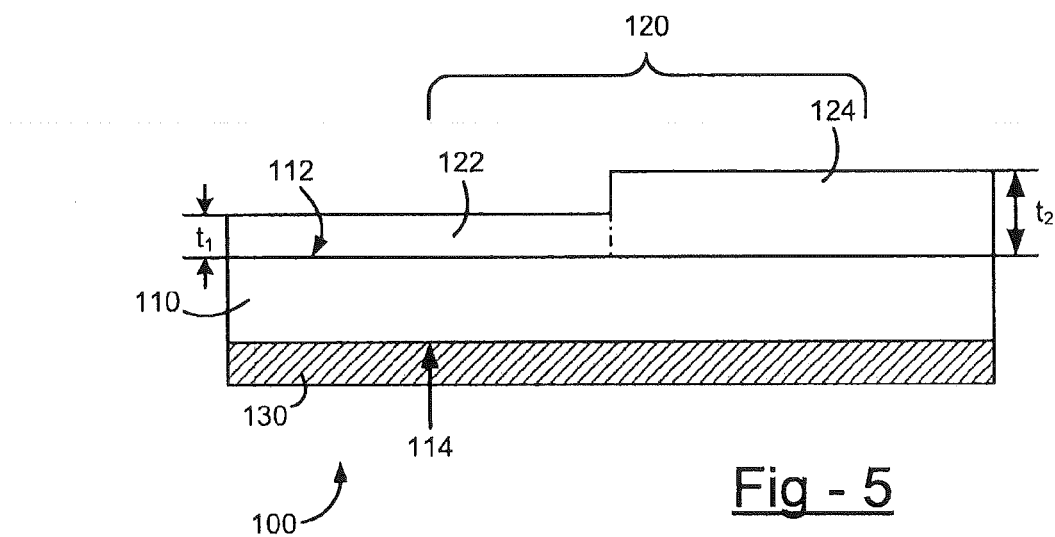
FIG. 5 is a schematic cross-sectional view of the exemplary X-ray detector of FIG. 4 taken along the line 5-5.

Referring now to FIGS. 4 and 5, an exemplary X-ray detector 100 according to some embodiments of the present disclosure is illustrated. Detector 100 includes a substrate 110, a scintillation layer 120 and a photosensor array 130 (such as a thin-film transistor, photodiode or similar). During operation of the imaging system 16, the X-ray source 36 will project a beam of X-ray radiation towards the X-ray detector 100. The scintillation layer 120 will convert the X-ray radiation into radiation at a different wavelength, such as visible light. The visible light will travel through the substrate 110 and be detected by the photosensor array 130. The photosensor array will convert the visible light into an electrical signal that can be detected and utilized by the computing system 32 to generate an image (such as displayed image data 18) of the patient 14.

The substrate 110 can have a first side 112 and a second side 114 opposite the first side 112. The substrate 110 can be a monolithic substrate made of glass or similar material. The monolithic construction of substrate 110 can reduce the amount of unintended distortion (scattering, reflection, refraction, diffraction, etc.) of the visible light generated by the scintillation layer 120.

The scintillation layer 120 can be arranged on the first side 112 of the substrate 110. In various embodiments, the scintillation layer 120 can be manufactured by depositing a scintillation material on the substrate 110, e.g., by physical vapor deposition, sputter deposition or other deposition technique. Examples of scintillation material include cesium iodide (CsI) and terbium doped gadolinium oxysulfide ($Gd_2O_2S:Tb$).

Figure 9:
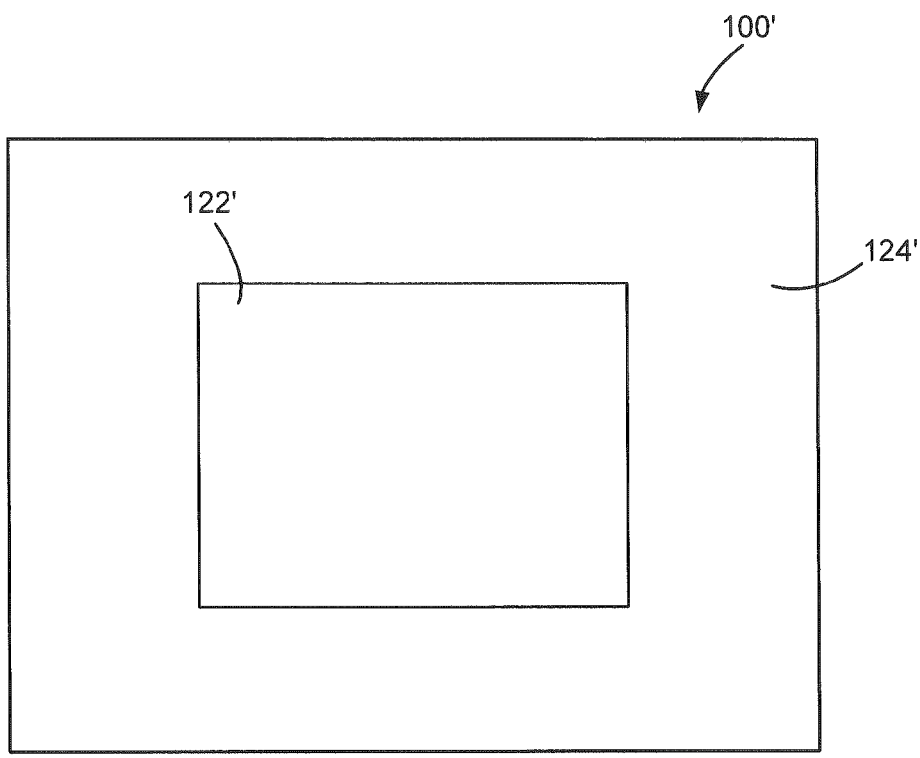
FIG. 9 is a schematic illustration of an exemplary X-ray detector of the imaging system of FIG. 1.
Figure 10:
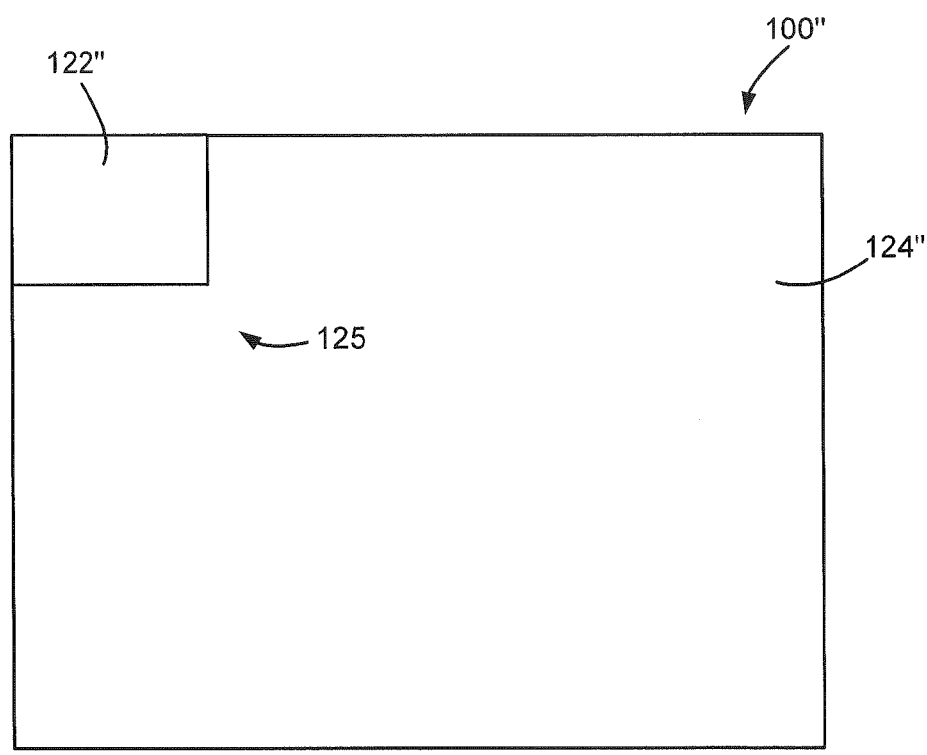
FIG. 10 is a schematic illustration of an exemplary X-ray detector of the imaging system of FIG. 1.

In some embodiments of the present disclosure, the X-ray detector 100 can include regions that have different X-ray sensitivities, e.g., by utilizing different scintillation materials for each region and/or varying the thickness of a single scintillation material across regions. In the illustrated example, the scintillation layer 120 includes a first region 122 having a first X-ray sensitivity and a second region 124 having a different second X-ray sensitivity. The first region 122 has a first thickness t1 of scintillation material and the second region 124 has a second thickness t2 of scintillation material that is different than the first thickness t1. The differing X-ray sensitivities of the first and second regions 122, 124 allow a user 12 to utilize the imaging system 16 to generate image data having different imaging characteristics/image qualities, as described below. While the illustrated example shows an X-ray detector 100 with a scintillation layer 120 that includes two different regions that are arranged side-by-side, it will be appreciated any number of regions greater than or equal to two may be utilized with the present disclosure. Additionally, the regions 122, 124 may be arranged other than side-by-side (e.g., an X-ray detector 100' having regions 122', 124', where the inner region 122' is surrounded by one or more outer regions 124', or an X-ray detector 100" having regions 122", 124", where the region 122" is confined to a corner portion 125 of the X-ray detector 100", etc.) without departing from the scope of the present disclosure. The X-ray detectors 100', 100" are shown in FIGS. 9-10.

The photosensor array 130 can be arranged upon the second side 114 of the substrate 110. The photosensor array 130 can be bonded to the second side 114, e.g., by adhesive or other bonding material. In some embodiments, the photosensor array 130 can be composed of a plurality of monolithic photosensor sub-arrays arranged next to each other. For example, referring now to FIG. 6, the photosensor array 130' can include a first monolithic photosensor sub-array 132 and a second monolithic photosensor sub-array 134 bonded together at a junction 135.

Figure 6:
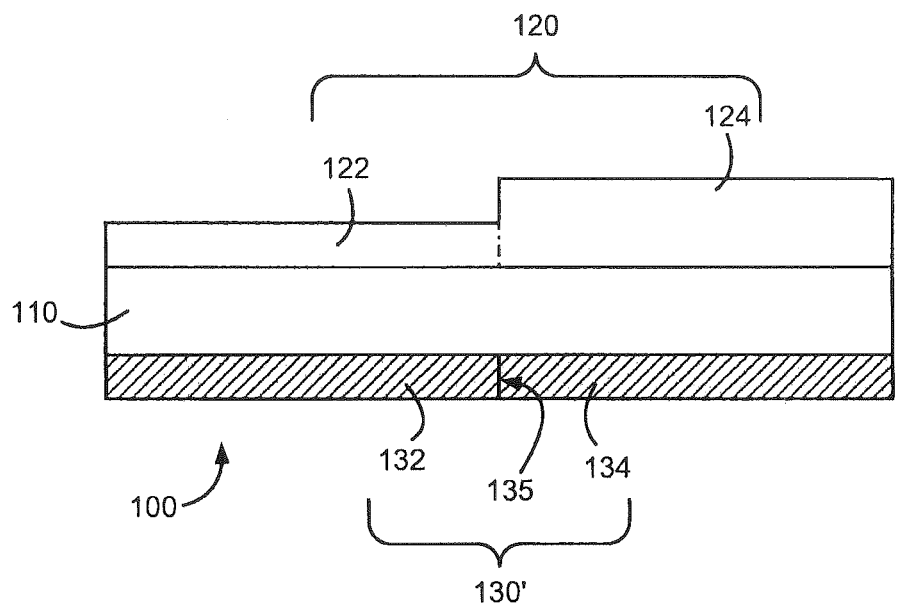
FIG. 6 is a schematic cross-sectional view of the exemplary X-ray detector of FIG. 4 taken along the line 5-5 showing an alternate construction.

In the illustrated example of FIG. 6, the first monolithic photosensor sub-array 132 corresponds to the first region 122 and the second monolithic photosensor sub-array 134 corresponds to the second region 124. In this manner, the first monolithic photosensor sub-array 132 can receive the radiation generated by the first region 122 and the second monolithic photosensor sub-array 134 can receive the radiation generated by the second region 124. Further, in some embodiments each of the monolithic photosensor sub-arrays 132, 134 can have a different set of performance parameters. The performance parameters for each of the monolithic photosensor sub-arrays 132, 134 can be chosen to correspond to the X-ray sensitivity of its associated region 122, 124. For example only, the first monolithic photosensor sub-array 132 can have a first set of performance parameters to correspond to the first X-ray sensitivity of the first region 122 and the second monolithic photosensor sub-array 134 can have a second set of performance parameters to correspond to the second X-ray sensitivity of the second region 124. The term "performance parameters" throughout this description can include, but is not limited to, the responsivity, dark current, noise-equivalent power, linearity of output, spectral response, quantum efficiency, light sensitivity, and/ or response time of a photosensor array.

Figure 7:
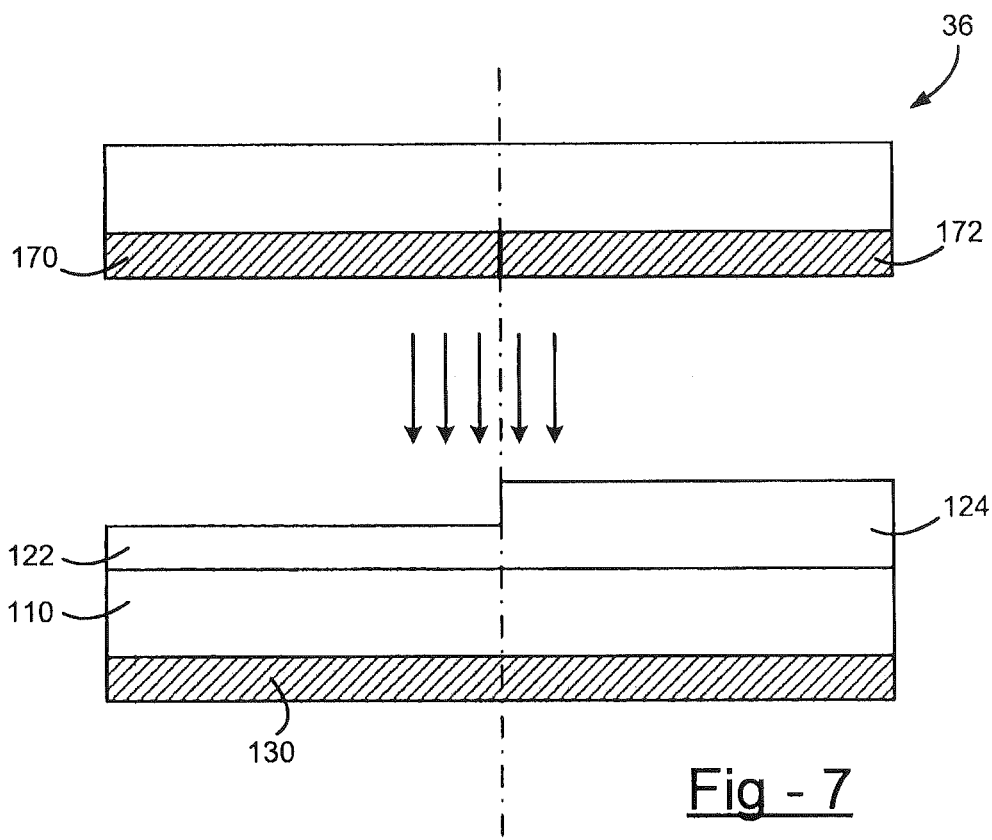
FIG. 7 is a schematic illustration of an exemplary X-ray source and an exemplary X-ray detector of the imaging system of FIG. 1.

In some embodiments of the present disclosure, the X-ray source 36 can include one or more filters (FIG. 7) arranged to filter the beam of X-ray radiation projected from the X-ray source 36. The filter(s) can be utilized to adapt the beam of X-ray radiation projected from the X-ray source 36 to correspond to the X-ray sensitivities of the regions 122, 124 of the X-ray detector 100 and/or the sets of performance parameters of the photosensor sub-arrays 132, 134 in order to improve the imaging characteristics/image quality of the image data. For example only, the X-ray source 36 can include a first filter 170 arranged to filter the beam of X-ray radiation received at the first region 122 of the X-ray detector 100 and a second filter 172 arranged to filter the beam of X-ray radiation received at the second region 124. The first filter 170 can have a first set of filtering characteristics and the second filter 172 can have a second set of filtering characteristics different than the first set. The term "filtering characteristics" throughout this description can include, but is not limited to, the frequencies and/or energy level(s) filtered out by a filter.

During operation of the imaging system 16, the X-ray source 36 projects a beam of X-ray radiation towards the X-ray detector 100 that has been positioned to receive the beam of X-ray radiation. The position of the X-ray source 36 and/or the X-ray detector 100 can be adjusted relative to one another in order to adjust the location 150 on the X-ray detector 100 that receives the beam of X-ray radiation. For examples, the beam of X-ray radiation can be received upon the entirety of the X-ray detector 100. Alternatively, the beam of X-ray radiation can be received upon only a portion of the X-ray detector 100. The user 12 can adjust, e.g., via computing system 32, the location 150 at which the X-ray detector 100 receives the beam of X-ray radiation based on the imaging characteristics/image quality desired by the user 12. The term "imaging characteristics" and/or "image quality" throughout this description can include, but are not limited to, varying levels of contrast, contrast sensitivity, dose efficiency, dose to patient, noise, artifacts, and/or distortion.

In some embodiments, the X-ray source 36 and X-ray detector 100 can be adjusted such that the location 150 at which the X-ray detector 100 receives the beam of X-ray radiation is primarily within either the first region 122 (FIG. 8A) or second region 124 (FIG. 8B). In this application, a location that receives a beam of X-ray radiation is considered to be received "primarily" within a region if more than 50% of the location is within that region. In some embodiments, the X-ray source 36 and X-ray detector 100 can be adjusted such that the location 150 at which the X-ray detector 100 receives the beam of X-ray radiation is more than 70%, more than 90% or entirely within either the first or second region 122, 124. In this manner, the imaging system 16 can take advantage of the different X-ray sensitivities of the first and second regions 122, 124 to image the patient 14. For example only, imaging low contrast regions of interest of a patient 14 (such as the soft tissue of the brain) may require substantially different imaging characteristics/ image quality than imaging high contrast regions (such as bone). With the present imaging system 16, the user 12 may utilize different regions (first region 122 or second region 124) of the X-ray detector 100 depending on the region of interest (soft tissue, bone, etc.) of the patient 14 to be imaged in order to provide the appropriate imaging characteristics/ image quality for the image data.

No matter what type of tissue (bony structure, soft tissue, etc.) to be imaged, the imaging system 16 can be utilized to generate image data with the appropriate imaging characteristics and/or image quality. The imaging system 16 (such as X-ray source 36 and/or X-ray detector 100) can be adjusted to adjust the location 150 to be primarily within one of the regions 122, 124 of the X-ray detector 100 depending on which region (122, 124) has the appropriate X-ray sensitivity for the subject of interest. For example, a region of interest 160 of the patient 14 can be positioned such that at least a portion of the beam of X-ray radiation passes through the region of interest 160 and impinges on the desired region 122, 124. In this manner, the patient 14 can be imaged to generate image data that has a first image quality (corresponding to one of the first and second regions 122, 124) for the region of interest 160 and a second image quality (corresponding to the other one of the first and second regions 122, 124) for a portion 165 of the patient 14 other than the region of interest 160.

An exemplary method of operating an X-ray imaging system, such as imaging system 16, according to various embodiments of the present disclosure can include providing an X-ray source 36 that is configured to project a beam of X-ray radiation. An X-ray detector 100 (as described above) can be positioned to receive the beam of X-ray radiation at a location 150. The method can also include adjusting the location 150 to correspond to a region of interest 160 of a patient 14 to be imaged. The location 150 can be adjusted such that at least a portion of the beam of X-ray radiation passes through the region of interest 160 and impinges primarily on, for example only, the first region 122. The patient 14 can be imaged to generate an image (such as displayed image data 18) of the patient 14. The image can have a first image quality for the region of interest 160 of the patient 14 and a second image quality for a portion of the patient 14 other than the region of interest 160. The first image quality can correspond to the first region 122 and the second image quality can correspond to the second region 124.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. An X-ray imaging system, comprising:
   a rotor configured to rotate about an object;
   an X-ray source mounted on the rotor and configured to project a beam of X-ray radiation toward the object;

a first filter arranged at the X-ray source to filter the beam of radiation prior to being received at a first region;
a second filter arranged at the X-ray source to filter the beam of radiation prior to being received at a second region; and
an X-ray detector mounted on the rotor and positioned to receive the beam of radiation, the X-ray detector including
a substrate having a first side and a second side,
a scintillation layer on the first side of the substrate, the scintillation layer having the first region with a first X-ray sensitivity and the second region with a second X-ray sensitivity different than the first X-ray sensitivity, and
a photosensor array on the second side of the substrate, the photosensor array having a first photosensor subarray that corresponds to the first region and a second photosensor subarray that corresponds to the second region,
wherein
the X-ray source is configured to pivot relative to the rotor and the X-ray detector between a first position and a second position to adjust a location at which the X-ray detector receives the beam of X-ray radiation,
when the X-ray source is pivoted to the first position, the location at which the X-ray detector receives the beam of radiation is adjusted such that the location is within the first region more than the second region, and
when the X-ray source is pivoted to the second position, the location at which the X-ray detector receives the beam of radiation is adjusted such that the location is within the second region more than the first region.

2. The X-ray imaging system of claim 1, wherein the X-ray source is configured to pivot relative to the X-ray detector between a first position and a second position to adjust the location at which the X-ray detector receives the beam of radiation.

3. The X-ray imaging system of claim 2, wherein when the X-ray source is pivoted to the first position, a majority of the location is within the first region and when the X-ray source is pivoted to the second position, a majority of the location is within the second region.

4. The X-ray imaging system of claim 1, wherein the X-ray detector is configured to translate about an arc relative to the X-ray source for acquisition of off-center image data.

5. The X-ray imaging system of claim 1, further comprising a gantry, wherein:
the rotor is rotationally positioned within the gantry; and
the X-ray source and the X-ray detector are coupled to the rotor such that the X-ray source can move in concert with the X-ray detector such that the X-ray source remains generally 180° apart from and opposed to the X-ray detector.

6. The X-ray imaging system of claim 1, wherein the first region of the scintillation layer has a first thickness and the second region of the scintillation layer has a second thickness different than the first thickness to provide the first and second X-ray sensitivities.

7. The X-ray imaging system of claim 1, wherein the substrate is a monolithic glass substrate to reduce an amount of distortion of a visible light generated by the scintillation layer.

8. The X-ray imaging system of claim 1, wherein the scintillation layer includes a scintillation material deposited on the first side of the substrate.

9. The X-ray imaging system of claim 1, wherein the X-ray source is configured to project a cone beam.

10. The X-ray imaging system of claim 1, wherein either (a) in a plane, the first region is completely surrounded by the second region, or (b) the first region is confined to only a single corner portion of the X-ray detector.

11. The X-ray imaging system of claim 1, wherein, in a plane, the first region is confined to only a single corner portion of the X-ray detector.

12. The X-ray imaging system of claim 1, wherein all portions of the scintillation layer having the first x-ray sensitivity are confined to a single corner portion of the X-ray detector.

13. The X-ray imaging system of claim 1, wherein:
the scintillation layer contacts the substrate; and
the substrate contacts the photosensor array.

14. An X-ray imaging system, comprising:
an annular gantry;
a rotor configured to rotate within the annular gantry and about an object;
an X-ray source pivotally mounted on the rotor and configured to project a beam of radiation toward the object, the X-ray source configured to pivot relative to the rotor between a first position and a second position to adjust a direction of the beam of radiation; and
an X-ray detector mounted on the rotor and positioned to receive the beam of radiation at a location, the X-ray detector including
a substrate having a first side and a second side opposite the first side,
a scintillation layer on the first side of the substrate, the scintillation layer having a first region with a first X-ray sensitivity and a second region with a second X-ray sensitivity different than the first X-ray sensitivity, and
a photosensor array on the second side of the substrate, wherein when the X-ray source is pivoted to the first position and relative to the rotor and the X-ray detector, a majority of the location is within the first region, and when the X-ray source is pivoted to the second position and relative to the rotor and the X-ray detector, a majority of the location is within the second region.

15. The X-ray imaging system of claim 14, wherein the X-ray detector is configured to be coupled to the rotor to translate about an arc relative to the rotor to enable an acquisition of off-center image data.

16. The X-ray imaging system of claim 14, wherein the substrate is glass and the scintillation layer includes scintillation material deposited on the glass.

17. The X-ray imaging system of claim 14, wherein:
the first region has a first thickness of scintillation material to provide the first X-ray sensitivity;
the second region has a second thickness of scintillation material; and
the second thickness is different than the first thickness to provide the second X-ray sensitivity.

18. The X-ray imaging system of claim 14, wherein the X-ray source and the X-ray detector are configured to adjust the location at which the X-ray detector receives the beam of X-ray radiation such that the location is entirely within the first region or the second region.

19. The X-ray imaging system of claim 14, wherein the X-ray source is configured to project a cone beam.

20. An imaging method for use with an X-ray imaging system, the imaging method comprising:
- rotating a rotor, that has a pivoting X-ray source and a translating X-ray detector attached thereto, relative to a patient;
- pivoting the X-ray source relative to the rotor and the X-ray detector while pivoting the X-ray source between (i) a first position to deliver an X-ray beam to a first region of the X-ray detector having a first X-ray sensitivity and (ii) a second position to deliver the X-ray beam to a second region of the X-ray detector having a second X-ray sensitivity; and
- imaging the patient to generate an image, where the image has
  - a first image quality for the first region of the X-ray detector, and
  - a second image quality for the second region of the X-ray detector.

21. The imaging method of claim 20, wherein the imaging includes passing the X-ray beam through a scintillation layer deposited on a glass layer, where a scintillation layer includes the first region and the second region.

22. The imaging method of claim 20, wherein the imaging includes passing the X-ray beam through the first region of a scintillation layer having a first thickness to provide the first X-ray sensitivity and the second region of the scintillation layer having a second thickness having the second X-ray sensitivity.

23. The imaging method of claim 20, further comprising rotating the rotor within an annular gantry.

24. The imaging method of claim 20, further comprising translating the X-ray detector to enable acquisition of off-center image data.

* * * * *

UNITED STATES PATENT AND TRADEMARK OFFICE
CERTIFICATE OF CORRECTION

PATENT NO.        : 9,880,293 B2
APPLICATION NO.   : 15/230720
DATED             : January 30, 2018
INVENTOR(S)       : Helm et al.

Page 1 of 1

It is certified that error appears in the above-identified patent and that said Letters Patent is hereby corrected as shown below:

Column 7, Line 62, Delete "32" and insert --22-- therefore;

Column 8, Line 20, Delete "t1" and insert --$t_1$-- therefore;

Column 8, Line 21, Delete "t2" and insert --$t_2$-- therefore;

Column 8, Line 22, Delete "t1" and insert --$t_1$-- therefore; and

Column 9, Line 38, Delete "32" and insert --22-- therefore.

Signed and Sealed this
Fifth Day of June, 2018

Andrei Iancu
*Director of the United States Patent and Trademark Office*